(12) United States Patent
Dicosimo et al.

(10) Patent No.: US 7,563,758 B2
(45) Date of Patent: Jul. 21, 2009

(54) **ENZYMATIC PRODUCTION OF PERACIDS USING *LACTOBACILLI* HAVING PERHYDROLYSIS ACTIVITY**

(75) Inventors: Robert Dicosimo, Chadds Ford, PA (US); L. Winona Wagner, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 302 days.

(21) Appl. No.: 11/524,870

(22) Filed: Sep. 21, 2006

(65) Prior Publication Data

US 2007/0184999 A1 Aug. 9, 2007

Related U.S. Application Data

(60) Provisional application No. 60/724,129, filed on Oct. 6, 2005.

(51) Int. Cl.
*C11D 3/386* (2006.01)
*C11D 3/395* (2006.01)
*C11D 3/39* (2006.01)
*C12P 7/62* (2006.01)
*C12P 7/64* (2006.01)

(52) U.S. Cl. .................. 510/305; 435/134; 435/135; 510/302; 510/306; 510/309; 510/310

(58) Field of Classification Search .............. None
See application file for complete search history.

(56) References Cited

U.S. PATENT DOCUMENTS 3,974,082 A 8/1976 Weyn
4,585,150 A 4/1986 Beacham et al.
5,296,161 A 3/1994 Wiersema et al.
5,364,554 A 11/1994 Stanislowski et al.
5,683,724 A 11/1997 Hei et al.
6,183,807 B1 2/2001 Gutzmann et al.
6,420,331 B1 * 7/2002 Bettiol et al. ............... 510/392
6,518,307 B2 2/2003 McKenzie et al.
6,545,047 B2 4/2003 Gutzmann et al.
2003/0026846 A1 2/2003 Hei et al.

FOREIGN PATENT DOCUMENTS

WO WO 2004/058961 A1 7/2004

OTHER PUBLICATIONS

U.S. Appl. No. 11/413,246, filed Apr. 28, 2006, DiCosimo et al.
Ole Kirk et. al., Enzyme Catalyzed Degradation and Formation of Peroxxycarboxylic Acids, Biocatalysis, 1994, vol. 11:65-77.
Stefan Minning et. al., Determination of Peracid and Putative Enzymatic Peracid Formation by an Easy Colorimetric Assay, Analytica Chimica Acta, 1999, 378:293-298.
U. Pinkernell et. al., Simultaneous HPLC Determination of Peroxyacetic Acid and Hydrogen Peroxide, Anal. Chem., 1997, vol. 69:3623-3627.
Jenny Gabrielson et. al., Evaluation of Redox Indicators and the Use of Digital Scanners and Spectrophotometer for Quantification of Microbial Growth in Microplates, J. Microbiol. Methods, 2002, vol. 50:63-73.

* cited by examiner

*Primary Examiner*—Herbert J. Lilling

(57) ABSTRACT

A method is provided for producing peroxycarboxylic acids from carboxylic acid esters. More specifically, carboxylic acid esters are reacted in situ with an inorganic peroxide such as hydrogen peroxide in the presence of a perhydrolase catalyst derived from a *Lactobacillus* sp. to produce peroxycarboxylic acids.

26 Claims, No Drawings

ENZYMATIC PRODUCTION OF PERACIDS USING *LACTOBACILLI* HAVING PERHYDROLYSIS ACTIVITY

This application claims the benefit of U.S. Provisional Application No. 60/724,129 filed Oct. 6, 2005.

FIELD OF THE INVENTION

This invention relates to the field of peracid biosynthesis and in situ enzyme catalysis. Specifically, *Lactobacillus* sp. having perhydrolysis activity were used to produce peracids from carboxylic acid ester substrates.

BACKGROUND OF THE INVENTION

Peracid compositions have been reported to be effective antimicrobial agents. Methods to clean, disinfect, and/or sanitize hard surfaces, meat products, living plant tissues, and medical devices against undesirable microbial growth have been described (U.S. Pat. Nos. 6,545,047, 6,183,807, 6,518, 307, US 20030026846, and U.S. Pat. No. 5,683,724). Peracids have also been reported to be useful in preparing bleaching compositions for laundry detergent applications (U.S. Pat. Nos. 3,974,082, 5,296,161, and 5,364,554).

Peracids can be prepared by the chemical reaction of a carboxylic acid and hydrogen peroxide (see *Organic Peroxides*, Daniel Swern, ed., Vol 1, pp 313-516; Wiley Interscience, New York). A strong inorganic acid, such as concentrated sulfuric acid, usually catalyzes the reaction. The reaction of hydrogen peroxide with a carboxylic acid is an equilibrium reaction, and the production of peracid is favored by the use of an excess concentration of peroxide and/or carboxylic acid, or by the removal of water. There are several disadvantages to the chemical reaction for peracid production: a) the high concentration of carboxylic acid used to favor production of peracid can result in an undesirable odor when using the peracid-containing solution, 2) the peracid is oftentimes unstable in solution over time, and the concentration of peracid in the solution decreases during storage prior to use, and 3) the formulation is often strongly acidic due to the use of concentrated sulfuric acid as catalyst.

One way to overcome the disadvantages of the chemical production of peracids is to employ an enzyme catalyst in place of a strong acid catalyst. The use of an enzyme catalyst allows for the rapid production of peracid at the time of use and/or application, avoiding problems associated with storage of peracid solutions and variations in peracid concentrations over time. The high concentrations of carboxylic acids typically used to produce peracid via the direct chemical reaction with hydrogen peroxide are not required for enzymatic production of peracid, where the enzyme catalyzed reaction can use a carboxylic acid ester substrate at a much lower concentration than is typically used in the chemical reaction. The enzyme reaction can be performed across a broad range of pH, dependent on enzyme activity and stability at a given pH, and on the substrate specificity for perhydrolysis at a given pH.

Esterases, lipases, and some proteases have the ability to catalyze the hydrolysis of alkyl esters to produce the corresponding carboxylic acids (Formula 1).

Formula 1

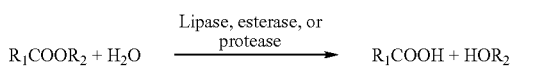

Some esterases, lipases and proteases exhibit perhydrolysis activity, catalyzing the synthesis of peracids from alkyl esters (Formula 2).

Formula 2

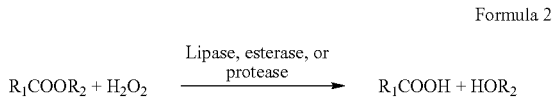

O. Kirk et al. (*Biocatalysis*, 11:65-77 (1994)) investigated the ability of hydrolases (lipases, esterases, and proteases) to catalyze perhydrolysis of acyl substrates with hydrogen peroxide to form peroxycarboxylic acids, and reported that perhydrolysis proceeds with a very low efficiency in aqueous systems. Furthermore, they found that lipases and esterases degraded percarboxylic acid to the corresponding carboxylic acid and hydrogen peroxide. The authors concluded that esterases, lipases and proteases are, in general, not suitable for catalyzing perhydrolysis of simple esters, such as methyl octanoate and trioctanoin, in an aqueous environment.

U.S. Pat. No. 3,974,082 describes the production of bleaching compositions for laundry detergent applications by contacting the material to be bleached with an aqueous solution containing an oxygen-releasing inorganic peroxygen compound, an acyl alkyl ester, and an esterase or lipase capable of hydrolyzing the ester.

U.S. Pat. No. 5,364,554 describes an activated oxidant system for in situ generation of peracid in aqueous solution using a protease enzyme, a source of hydrogen peroxide, and an ester substrate that is preferably chemically non-perhydrolyzable. A method of bleaching and a method of forming peracid are also disclosed.

U.S. Pat. No. 5,296,161 describes production of peracid in an aqueous solution comprising one or more specific esterases and lipases, a source of hydrogen peroxide, and a functionalized ester substrate suitable for use in a bleaching composition. However, the concentration of peracid produced was generally insufficient for use in many commercial disinfectant applications.

Most known methods for preparing peracids from the corresponding carboxylic acid esters using enzyme catalysts do not produce and accumulate a peracid at a sufficiently-high concentration to be efficacious for disinfection in a variety of applications. Several protease and lipase combinations have recently been reported to generate peracids (e.g. peracetic acid) in situ at concentrations suitable for use as a disinfectant and/or commercial bleaching agent (U.S. Ser. No. 11/413, 246). However, there remains a need to identify additional perhydrolase catalysts capable of producing peracids in situ.

The pH of disinfectant compositions has been reported to affect both biocidal and/or virucidal activity. Some disinfectant compositions optimally function under acidic conditions. However, many enzymes having perhydrolytic activity for carboxylic acid ester substrate optimally work under somewhat neutral pH. Hence, there is a need to identify perhydrolase catalysts that can generate peracids in situ under acidic conditions.

The problem to be solved is to provide a process to enzymatically produce peracids in situ at concentrations suitable for use in a variety of disinfectant applications. Preferably, the substrates used to produce the peracid compositions should be relatively non-toxic and inexpensive, such as carboxylic acid esters. In a further aspect of the problem, the process uses perhydrolase catalysts able to produce peracids in situ under acidic reaction conditions at concentrations suitable for use as a disinfectant and/or bleaching agent.

SUMMARY OF THE INVENTION

The stated problem has been solved by the discovery that *Lactobacillus* sp., in the presence of an inorganic source of peroxygen (e.g. hydrogen peroxide), have perhydrolysis activity for converting carboxylic acid ester substrates into peracids in situ at concentrations sufficient for use as a disinfectant and/or bleaching agent.

In one aspect of the invention, an aqueous enzymatic process for in situ generation of peracids using a perhydrolytic activity derived from a *Lactobacillus* sp. in combination with selected substrates is provided comprising:

a) providing a set of peracid reaction components, said components comprising:

1. a substrate selected from the group consisting:

i) esters having the structure

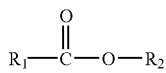

wherein $R_1$=C1 to C10 straight chain or branched chain alkyl optionally substituted with an hydroxyl or C1 to C4 alkoxy group and $R_2$=C1 to C10 straight chain or branched chain alkyl group, $(CH_2CH_2-O)_nH$ or $(CH_2CH(CH_3)-O)_nH$ and n=1 to 10;

ii) glycerides having the structure

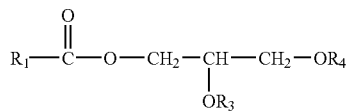

wherein $R_1$=C1 to C10 straight chain or branched chain alkyl optionally substituted with an hydroxyl or a C1 to C4 alkoxy group and $R_3$ and $R_4$ are individually H or $R_1C(O)$;

2) a source of peroxygen; and 3) a perhydrolysis activity derived from a *Lactobacillus* sp.;

b) combining said reaction components under suitable aqueous reaction conditions whereby a peracid composition is produced comprising of a peracid concentration of at least 500 ppb within about 5 minutes to about 2 hours of combining the reaction components. In another aspect, the present method to generate peracids in situ is conducted under acidic reaction conditions.

In another aspect of the invention, a method is provided to reduce a viable microbial population on a hard surface or inanimate object by contacting the peracid composition produced by the above method with a hard surface or inanimate object within about 48 hours of mixing the peracid reaction components whereby the viable microbial population is reduced at least 3-log, preferably at least 4-log, more preferably at least 5-log, and most preferably at least 6-log. In a further aspect, the peracid composition produced by the above methods may be optionally diluted to a desired efficacious concentration prior to contacting the surface or inanimate object to be treated. In a further aspect, the present peracid compositions are produced in situ under acidic reaction conditions.

DETAILED DESCRIPTION OF THE INVENTION

The stated problem has been solved by the discovery that *Lactobacillus* sp., in the presence of an inorganic source of peroxygen (e.g. hydrogen peroxide), have perhydrolysis activity for carboxylic acid ester substrates, generating concentrations of peracids in situ sufficient for disinfection and/or bleaching applications. As such, a process is provided for in situ generation of peracids from a carboxylic acid ester substrate using perhydrolase activity derived from a *Lactobacillus* sp. In one aspect, the process for in situ generation of peracids using perhydrolysis activity derived from a *Lactobacillus* sp. occurs under acidic reaction conditions.

In this disclosure, a number of terms and abbreviations are used. The following definitions apply unless specifically stated otherwise.

As used herein, the term "comprising" means the presence of the stated features, integers, steps, or components as referred to in the claims, but that it does not preclude the presence or addition of one or more other features, integers, steps, components or groups thereof.

As used herein, the term "about" modifying the quantity of an ingredient or reactant of the invention or employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, the term "peracid" is synonymous with peroxyacid, peroxycarboxylic acid, peroxy acid, percarboxylic acid and peroxoic acid.

As used herein, the term "peracetic acid" is abbreviated as "PAA" and is synonymous with peroxyacetic acid, ethaneperoxoic acid and all other synonyms of CAS Registry Number 79-21-0.

As used herein, the term "a source of peroxygen" means a peroxygen compound (i.e., a "peroxygen source") capable of providing hydrogen peroxide to the aqueous reaction mixture selected from the group consisting of perborate salts, percarbonate salts, perphosphate salts, hydrogen peroxide, hydrogen peroxide-urea adduct (CAS# 124-43-6), and mixtures thereof.

As used herein, the term "monoacetin" is synonymous with glycerol monoacetate, glycerin monoacetate, and glyceryl monoacetate.

As used herein, the term "diacetin" is synonymous with glycerol diacetate; glycerin diacetate, glyceryl diacetate, and all other synonyms of CAS Registry Number 25395-31-7.

As used herein, the term "triacetin" is synonymous with glycerin triacetate; glycerol triacetate; glyceryl triacetate, 1,2,3-triacetoxypropane, 1,2,3-propanetriol triacetate and all other synonyms of CAS Registry Number 102-76-1.

As used herein, the term "monobutyrin" is synonymous with glycerol monobutyrate, glycerin monobutyrate, and glyceryl monobutyrate.

As used herein, the term "dibutyrin" is synonymous with glycerol dibutyrate and glyceryl dibutyrate.

As used herein, the term "tributyrin" is synonymous with glycerol tributyrate, 1,2,3-tributyrylglycerol, and all other synonyms of CAS Registry Number 60-01-5.

As used herein, the term "monopropionin" is synonymous with glycerol monopropionate, glycerin monopropionate, and glyceryl monopropionate.

As used herein, the term "dipropionin" is synonymous with glycerol dipropionate and glyceryl dipropionate.

As used herein, the term "tripropionin" is synonymous with glyceryl tripropionate, glycerol tripropionate, 1,2,3-tripropionylglycerol, and all other synonyms of CAS Registry Number 139-45-7.

As used herein, the term "ethyl acetate" is synonymous with acetic ether, acetoxyethane, ethyl ethanoate, acetic acid ethyl ester, ethanoic acid ethyl ester, ethyl acetic ester and all other synonyms of CAS Registry Number 141-78-6.

As used herein, the term "ethyl lactate" is synonymous with lactic acid ethyl ester and all other synonyms of CAS Registry Number 97-64-3.

As used herein, the term "suitable aqueous reaction conditions" refers to the conditions in which the reactants and perhydrolase catalyst come into contact. The components and conditions suitable for reaction are provided herein and those skilled in the art appreciate the range of component and condition variations suitable for the processes.

As used herein, the term "perhydrolysis" is defined as the reaction of a selected substrate with peroxide to form a peracid. Typically, an inorganic peroxide is reacted with the selected substrate in the presence of a catalyst to produce the peracid. As used herein, the term "chemical perhydrolysis" includes perhydrolysis reactions in which a substrate (a peracid precursor) is combined with a source of hydrogen peroxide wherein peracid is formed in the absence of an enzyme catalyst.

As used herein, the term "perhydrolase catalyst" refers herein to an enzyme catalyst that is characterized by perhydrolysis activity. The enzyme catalyst may be in the form of a whole microbial cell, permeabilized microbial cell(s), one or more cell components of a microbial cell extract, partially purified enzyme, or purified enzyme. As described herein, perhydrolase catalysts are shown to have perhydrolysis activity towards carboxylic acid esters. In one preferred aspect, the perhydrolase catalyst is derived from a *Lactobacillus* sp. In a further aspect, the *Lactobacillus* sp.-derived catalyst is in the form of a whole cell, permeabilized cell, or a microbial cell extract. In yet a further aspect, the perhydrolase catalyst is in the form of a whole microbial cell. The perhydrolase catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997.

As used herein, "*Lactobacillus* sp." or "*Lactobacilli* sp." refers to members of the genera *Lactobacillus*. Most members of this group are characterized by their ability to produce a significant amount of lactic acid when grown on glucose. They are known to be rather resistant to acidic conditions, typically growing well at a pH value of about 5. *Lactobacilli* are most commonly used for the preparation of fermented dairy products and are almost never pathogenic.

Many *Lactobacillus* sp. have been reported to have hydrolase activity towards a variety of substrates. As described herein, *Lactobacillus* sp. are provided that exhibit perhydrolysis activity under suitable aqueous reaction conditions towards a variety of carboxylic acid esters, producing significant concentrations of peracids in situ.

As used herein, the term "perhydrolase activity" refers to the catalyst activity per unit mass (for example, milligram) of protein, dry cell weight, or immobilized catalyst weight. Comparisons of perhydrolase activity of catalysts were determined proportional to the dry cell weight or protein catalyst weight.

As used herein, "one unit of enzyme activity" or "one unit of activity" or "U" is defined as the amount of perhydrolase activity required for the production of 1 μmol of peracid product per minute at a specified temperature.

As used herein, the term "disinfect" refers to the process of cleansing so as to destroy and prevent the growth of pathogenic microorganisms. As used herein, the term "disinfectant" refers to an agent that disinfects by destroying, neutralizing, or inhibiting the growth of disease-carrying microorganisms. Typically disinfectants are used to treat inanimate objects or surfaces. As used herein, the term "antiseptic" refers to a chemical agent that inhibits the growth of disease-carrying microorganisms.

As used herein, the terms "virucide" and "viricide" refer to an agent that inhibits or destroys viruses. An agent that exhibits the ability to inhibit or destroy viruses is described as having "virucidal" activity. Peracids can have virucidal activity. Typical alternative virucides known in the art that may be suitable for use with the present invention include, for example, alcohols, ethers, chloroform, formaldehyde, phenols, beta propiolactone, iodine, chlorine, mercury salts, hydroxylamine, ethylene oxide, ethylene glycol, quaternary ammonium compounds, enzymes, and detergents.

As used herein, the term "biocide" refers to a chemical agent, typically broad spectrum, which inactivates or destroys microorganisms. A chemical agent that exhibits the ability to inactivate or destroy microorganisms is described as having "biocidal" activity. Peracids can have biocidal activity. Typical alternative biocides known in the art, that may be suitable for use in the present invention include, for example, chlorine, chlorine dioxide, chloroisocyanurates, hypochlorites, ozone, acrolein, amines, chlorinated phenolics, copper salts, organosulphur compounds, and quaternary ammonium salts.

As used herein, the phrase "minimum biocidal concentration" refers to the minimum concentration of a biocidal agent that, for a specific contact time, will produce a desired lethal, irreversible reduction in the viable population of the targeted microorganisms. The effectiveness can be measured by the $\log_{10}$ reduction in viable microorganisms after treatment. In one aspect, the targeted reduction in viable cells after treatment is a 3-log reduction, more preferably a 4-log reduction, and most preferably at least a 5-log reduction. In another aspect, the minimum biocidal concentration is a 6-log reduction in viable microbial cells.

Suitable Reaction Conditions for the Enzyme-catalyzed Preparation of Peracids from Carboxylic Acid Esters and Hydrogen Peroxide In one aspect of the invention, a method is provided to produce an aqueous mixture comprising a peracid by reacting carboxylic acid esters and an inorganic peroxide, not limited to hydrogen peroxide, sodium perborate or sodium percarbonate, in the presence of a *Lactobacillus* sp.-derived catalyst having perhydrolysis activity.

Suitable carboxylic acid ester substrates have a formula selected from the group consisting of:
a) esters of the formula

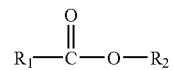

wherein $R_1$=C1 to C10 straight chain or branched chain alkyl optionally substituted with an hydroxyl or a C1 to C4 alkoxy group and $R_2$=C1 to C10 strain chain or branched chain alkyl group, $(CH_2CH_2-O)_nH$ or $(CH_2CH(CH_3)-O)_nH$ and n=1 to 10; and b) glycerides of the formula

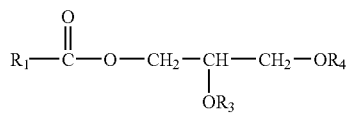

wherein $R_1$=C1 to C10 straight chain or branched chain alkyl optionally substituted with an hydroxyl or a C1 to C4 alkoxy group and $R_3$ and $R_4$ are individually H or $R_1C(O)$; and In one aspect, the carboxylic acid ester substrates are selected from the group consisting of methyl lactate, ethyl lactate, methyl glycolate, ethyl glycolate, methyl methoxyacetate, ethyl methoxyacetate, methyl 3-hydroxybutyrate, ethyl 3-hydroxybutyrate, triethyl 2-acetyl citrate, glucose pentaacetate, gluconolactone, glycerides (mono-, di-, and triglycerides) such as monoacetin, diacetin, triacetin, monopropionin, dipropionin (glyceryl dipropionate), tripropionin (1,2,3-tripropionylglycerol), monobutyrin, dibutryin (glyceryl dibutyrate), tributyrin (1,2,3-tributyrylglycerol), and mixtures thereof. In another aspect, the carboxylic acid ester substrates are selected from the group consisting of monoacetin, diacetin, triacetin, monpropionin, dipropionin, tripropionin, monobutyrin, dibutyrin, tributyrin, ethyl acetate, and ethyl lactate. In yet another aspect, the carboxylic acid ester substrates are selected from the group consisting of diacetin, triacetin, ethyl acetate, and ethyl lactate.

The carboxylic acid ester substrate is present in the reaction mixture at a concentration sufficient to produce the desired concentration of peracid upon enzyme-catalyzed perhydrolysis. The carboxylic acid ester need not be completely soluble in the reaction mixture, but have sufficient solubility to permit conversion of the ester by the perhydrolase catalyst to the corresponding peracid. The carboxylic acid ester substrate is present in the reaction mixture at a concentration of 0.05 wt % to 40 wt % of the reaction mixture, preferably at a concentration of 0.1 wt % to 20 wt % of the reaction mixture, and more preferably at a concentration of 0.5 wt % to 10 wt % of the reaction mixture.

The peroxygen source may include, but is not limited to, hydrogen peroxide, perborate salts, perphosphate salts, percarbonate salts, hydrogen peroxide-urea adduct, and mixtures thereof. The concentration of peroxygen compound in the reaction mixture may range from 0.1 wt % to about 50 wt %, preferably from 1 wt % to about 40 wt %, more preferably from 2 wt % to about 30 wt %.

Many perhydrolase catalysts (whole cell, permeabilized whole cells, and partially purified whole cell extracts) have been reported to have catalase activity (EC 1.11.1.6). Catalases catalyze the conversion of hydrogen peroxide into oxygen and water. In one aspect, the perhydrolysis catalyst lacks catalase activity. In another aspect, a catalase inhibitor is added to the reaction mixture. Examples of catalase inhibitors include, but are not limited to, sodium azide and hydroxylamine sulfate. One of skill in the art can adjust the concentration of catalase inhibitor as needed. The concentration of the catalase inhibitor typically ranges from 0.1 mM to about 1 M; preferably about 1 mM to about 50 mM; more preferably from about 1 mM to about 20 mM. In one aspect, sodium azide concentration typically ranges from about 20 mM to about 60 mM while hydroxylamine sulfate concentration is typically about 0.5 mM to about 30 mM, preferably about 10 mM. In a preferred embodiment, the enzyme catalyst lacks significant catalase activity or is engineered to decrease or eliminate catalase activity. In a further embodiment, the catalase activity in a host cell can be down-regulated or eliminated by disrupting expression of the gene(s) responsible for the catalase activity using well known techniques including, but not limited to, transposon mutagenesis, RNA antisense expression, targeted mutagenesis, and random mutagenesis.

The concentration of the catalyst in the aqueous reaction mixture is chosen to obtain the desired rate of reaction, and depends on the specific catalytic activity of the catalyst. The weight of catalyst in perhydrolysis reactions typically ranges from 0.05 mg to 10 mg per mL of total reaction volume, preferably from 0.10 mg to 2.0 mg per mL. The catalyst may also be immobilized on a soluble or insoluble support using methods well-known known to those skilled in the art; see for example, *Immobilization of Enzymes and Cells*; Gordon F. Bickerstaff, Editor; Humana Press, Totowa, N.J., USA; 1997. The use of immobilized catalysts permits the recovery and reuse of the catalyst in subsequent reactions. The perhydrolase catalyst (derived from one or more *Lactobacillus* sp.) may be in the form of whole microbial cells, permeabilized microbial cells, microbial cell extracts, partially-purified or purified enzymes, and mixtures thereof.

In one aspect, the concentration of peracid generated by the combination of chemical perhydrolysis and enzymatic perhydrolysis of the carboxylic acid ester is sufficient to provide an effective concentration of peracid for bleaching or disinfection at a desired pH. In another aspect, the present methods provide combinations of enzymes and enzyme substrates to produce the desired effective concentration of peracid, where, in the absence of added enzyme, there is a significantly lower concentration of peracid produced. Although there may in some cases be significant chemical perhydrolysis of the enzyme substrate by direct chemical reaction of inorganic peroxide with the enzyme substrate, there may not be a sufficient concentration of peracid generated by chemical perhydrolysis to provide an effective concentration of peracid in the desired applications, and a significant increase in total peracid concentration is achieved by the addition of an appropriate perhydrolase catalyst to the reaction mixture.

The concentration of peracid generated by the perhydrolysis of at least one carboxylic acid ester substrate is at least 500 ppb peracid, preferably at least 1.5 ppm peracid, more preferably at least 2.5 ppm peracid, even more preferably at least 4.5 ppm peracid, and most preferably at least 7.5 ppm. The product mixture comprising the peracid may be optionally diluted with water, or a solution predominantly comprised of water, to produce a mixture with the desired lower concentration of peracid. In one aspect, the reaction time required to produce the desired concentration of peracid is not greater than about two hours, preferably not greater than about 30 minutes, more preferably not greater than about 10 minutes, and most preferably less than about 5 minutes. In another aspect, the peracid concentration may continue to increase above the initial desired concentration of peracid generated in not greater than about 2 hours, such that the reaction mixture produces a maximum concentration of peracid in at least 48 hours.

The temperature of the reaction is chosen to control both the reaction rate and the stability of the enzyme catalyst activity. The temperature of the reaction may range from just above the freezing point of the reaction mixture (approximately 0° C.) to about 65° C., with a preferred range of reaction temperature of from about 5° C. to about 35° C.

The pH of the final reaction mixture containing peracid is from about 1.0 to about 10, preferably from about 2.0 to about 9.0, more preferably from about 3.5 to about 7.0, and even more preferably about 3.5 to about 6.5. In one embodiment, the pH of the reaction mixture is acidic (pH<7.0). In another embodiment, the pH of the reaction mixture is less than about 5.5, preferably less than about 4.5, and most preferably less than about 4.0. The pH of the reaction, and of the final reaction mixture, may be controlled by the addition of a suitable buffer, including, but not limited to phosphate, pyrophosphate, bicarbonate, acetate, or citrate. The concentration of buffer is from 0.1 mM to 1.0 M, preferably from 1 mM to 100 mM, most preferably from 10 mM to 50 mM.

In another aspect, the perhydrolysis product may contain additional components that provide desirable functionality. In one aspect, the desirable functionality may include use of the present materials in bleaching applications. These additional components include, but are not limited to emulsifiers and surfactants. Examples of emulsifiers include polyvinyl alcohol or polyvinylpyrrolidine. Examples of surfactants, including a) non-ionic surfactants such as block copolymers of ethylene oxide or propylene oxide, ethoxylated or propoxylated linear and branched primary and secondary alcohols, and aliphatic phosphine oxides b) cationic surfactants such as such as quaternary ammonium compounds, particularly quaternary ammonium compounds having a C8-C20 alkyl group bound to a nitrogen atom additionally bound to three C1-C2 alkyl groups, c) anionic surfactants such as alkane carboxylic acids (e.g., C8-C20 fatty acids), alkyl phosphonates, alkane sulfonates (e.g., sodium dodecylsulphate) or linear or branched alkyl benzene sulfonates, alkene sulfonates and d) amphoteric and zwitterionic surfactants such as aminocarboxylic acids, aminodicarboxylic acids, and alkybetaines. Additional components may include fragrances, dyes, stabilizers of hydrogen peroxide (e.g., 1-hydroxyethylidene-1,1,-diphosphonic acid (Dequest 2010, Solutia Inc., St. Louis, Mo.)), stabilizers of enzyme activity (e.g., polyethyleneglycol (PEG)), detergent builders and metal chelators (e.g., ethylenediaminetetraacetic acid (EDTA)).

In Situ Production of Peracids Using a Perhydrolase Catalyst

The present method produces industrially-useful concentrations of peracids in situ under aqueous reaction conditions using perhydrolase activity derived from one or more *Lactobacillus* sp. The peracids produced are quite reactive and unstable, generally decreasing in concentration over time. As such, it may be desirable to keep the various reaction components separated, especially for liquid formulations. In one aspect, the hydrogen peroxide source is separate from either the substrate or the perhydrolase catalyst, preferably from both. This can be accomplished using a variety of techniques including, but not limited to the use of multicompartment chambered dispensers (U.S. Pat. No. 4,585,150) and physically combining the perhydrolase catalyst with the present substrates to initiate the aqueous enzymatic perhydrolysis reaction. The perhydrolase catalyst may be immobilized within the body of reaction chamber or separated (e.g. filtered, etc.) from the reaction product comprising the peracid prior to contacting the surface and/or object targeted for treatment. The perhydrolase catalyst may be in a liquid matrix or in a solid form (i.e. powdered, tablet) or embedded within a solid matrix that is subsequently mixed with the substrates to initiate the enzymatic perhydrolysis reaction. In a further aspect, the perhydrolase catalyst may be contained within a dissolvable or porous pouch that may be added to the aqueous substrate matrix to initiate enzymatic perhydrolysis.

HPLC Assay Method for Determining the Concentration of Peracid and Hydrogen Peroxide.

A variety of analytical methods can be used in the present method to analyze the reactants and products including, but not limited to titration, high performance liquid chromatography (HPLC), gas chromatography (GC), mass spectroscopy (MS), capillary electrophoresis (CE), and the 2,2'-azino-bis(3-ethylbenzothazoline)-6-sulfonate (ABTS) assay (S. Minning, et al., *Analytica Chimica Acta* 378:293-298 (1999) and WO 2004/058961 A1) as described in the present examples.

The HPLC analytical procedure described by U. Karst et al. (*Anal. Chem.*, 69 (17):3623-3627 (1997)) was employed, as described herein, for analysis of product mixtures containing peracid and hydrogen peroxide. Briefly, the concentration of peracetic acid (PAA) in analyzed samples ranged from 0.025 mM-10 mM, and the concentration of $H_2O_2$ ranged from 0.075 mM-3 mM. Reaction mixtures containing peracid and/or hydrogen peroxide were, if necessary prior to analysis, diluted to produce a concentration of peracid or peroxide in these ranges. Into a 4-mL vial was placed 0.100 mL of 20 mM methyl p-tolyl sulfide (MTS) in acetonitrile, 0.300 mL of distilled and deionized water (dd) and 0.100 mL of sample solution (undiluted or diluted with dd water by a factor of up to 1:25 for analysis of peracid), or 0.100 mL of 20 mM MTS in acetonitrile and 0.390 mL of dd water were added to 0.010 mL of a 1:10 dilution of sample solution (for analysis of hydrogen peroxide). After a reaction time of 10 minutes (in the dark, with no stirring), 0.400 mL $CH_3CN$ and 0.100 mL of 40-mM triphenylphosphine (TPP) in $CH_3CN$ were added to start the second derivatization reaction for detection of peroxide. The solution was left standing in the dark for 30 min to complete the assay reaction. At the end of 30 minutes, 0.100 mL of 10 mM N,N-diethyl-m-toluamide (DEET, HPLC external standard) was added and the resulting solution analyzed by HPLC: Supelco Discovery C8 10-cm column with pre-column, 10-µL injection, UV detection at 225 nm, solvent A: acetonitrile, solvent B: deionized water, 1 mL/min gradient as follows:

| Time (min:sec) | % $CH_3CN$ | % $H_2O$ |
|---|---|---|
| 0:00 | 40 | 60 |
| 3:00 | 40 | 60 |
| 3:10 | 100 | 0 |
| 4:00 | 100 | 0 |
| 4:10 | 40 | 60 |
| 7:00 (stop) | 40 | 60 |

Determination of Minimum Biocidal Concentration of Peracids

The method described by J. Gabrielson, et al. (*J. Microbiol. Methods* 50: 63-73 (2002)) can be employed for determination of the Minimum Biocidal Concentration (MBC) of peracids, or of hydrogen peroxide and enzyme substrates. The assay method is based on XTT reduction inhibition, where XTT ((2,3-bis[2-methoxy-4-nitro-5-sulfophenyl]-5-[(phenylamino)carbonyl]-2H-tetrazolium, inner salt, monosodium salt) is a redox dye that indicates microbial respiratory activity by a change in optical density (OD) measured at 490 nm or 450 nm. However, there are a variety of other methods available for testing the activity of disinfectants and antiseptics including, but not limited to viable plate counts, direct microscopic counts, dry weight, turbidity measurements, absorbance, and bioluminescence (see, for example Brock, Semour S., *Disinfection, Sterilization, and Preservation*, 5th edition, Lippincott Williams & Wilkins, Philadelphia, Pa., USA; 2001).

Uses of Enzymatically Prepared Peracid Compositions

The enzyme catalyst generated peracid produced according to the present methods can be used in a variety of applications for reduction of microbial, fungal, and viral contamination, such as decontamination of medical instruments (e.g., endoscopes), textiles (e.g., garments, carpets), food preparation surfaces, food storage and food-packaging equipment, materials used for the packaging of food products, chicken hatcheries and grow-out facilities, animal enclosures, and spent process waters that have microbial and/or virucidal activity. The enzyme-generated peracids may be used in formulations designed to inactivate prions (e.g. a formulation containing certain proteases) to additionally provide biocidal activity. In a preferred aspect, the present peracid compositions are particularly useful as a cleaning and disinfecting agent for non-autoclavable medical instruments and food packaging equipment. As the peracid-containing formulation may be prepared using GRAS or food-grade components (enzyme, enzyme substrate, hydrogen peroxide, and buffer), the enzyme-generated peracid may also be used for decontamination of animal carcasses, meat, fruits and vegetables, or for decontamination of prepared foods. The enzyme-generated peracid may be incorporated into a product whose final form is a powder, liquid, gel, solid or aerosol. The enzyme-generated peracid may be diluted to a concentration that still provides an efficacious decontamination.

The compositions comprising an efficacious concentration of peracid can be used to clean and disinfect surfaces and/or objects contaminated (or suspected of being contaminated) with pathogenic microorganisms and/or viruses by contacting the surface or object with the products produced by the present processes. As used herein, "contacting" refers to placing a disinfecting composition comprising an effective concentration of peracid in contact with the surface or inanimate object suspected of contamination with a disease-causing entity for a period of time sufficient to clean and disinfect. Contacting includes spraying, treating, immersing, flushing, pouring on or in, mixing, combining, painting, coating, applying, affixing to and otherwise communicating a peracid solution comprising an efficacious concentration of peracid with the surface or inanimate object suspected of being contaminated.

The compositions comprising an efficacious concentration of peracid can also contain an additional antimicrobial agent, virucide or biocide. Combinations of these agents with the peracid produced by the claimed processes can provide for increased and/or synergistic effects when used to clean and disinfect surfaces and/or objects contaminated (or suspected of being contaminated) with pathogenic microorganisms, viruses, and/or prions. Suitable antimicrobial agents include carboxylic esters (e.g., p-hydroxy alkyl benzoates and alkyl cinnamates), sulfonic acids (e.g., dodecylbenzene sulfonic acid), iodo-compounds or active halogen compounds (e.g., elemental halogens, halogen oxides (e.g., NaOCl, HOCl, HOBr, $ClO_2$), iodine, interhalides (e.g., iodine monochloride, iodine dichloride, iodine trichloride, iodine tetrachloride, bromine chloride, iodine monobromide, or iodine dibromide), polyhalides, hypochlorite salts, hypochlorous acid, hypobromite salts, hypobromous acid, chloro- and bromo-hydantoins, chlorine dioxide, and sodium chlorite), organic peroxides including benzoyl peroxide, alkyl benzoyl peroxides, ozone, singlet oxygen generators, and mixtures thereof, phenolic derivatives (e.g., o-phenyl phenol, o-benzyl-p-chlorophenol, tert-amyl phenol and $C_1$-$C_6$ alkyl hydroxy benzoates), quaternary ammonium compounds (e.g., alkyldimethylbenzyl ammonium chloride, dialkyldimethyl ammonium chloride and mixtures thereof), and mixtures of such antimicrobial agents, in an amount sufficient to provide the desired degree of microbial protection. Effective amounts of antimicrobial agents include about 0.001 wt-% to about 60 wt-% antimicrobial agent, about 0.01 wt-% to about 15 wt-% antimicrobial agent, or about 0.08 wt-% to about 2.5 wt-% antimicrobial agent.

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

GENERAL METHODS

The following examples are provided to demonstrate preferred aspects of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All reagents and materials were obtained from DIFCO Laboratories (Detroit, Mich.), GIBCO/BRL (Gaithersburg, Md.), TCI America (Portland, Oreg.), Roche Diagnostics Corporation (Indianapolis, Ind.) or Sigma/Aldrich Chemical Company (St. Louis, Mo.), unless otherwise specified.

The following abbreviations in the specification correspond to units of measure, techniques, properties, or compounds as follows: "sec" or "s" means second(s), "min" means minute(s), "h" or "hr" means hour(s), "d" means density in g/mL, "µL" means microliters, "mL" means milliliters, "L" means liters, "mM" means millimolar, "M" means molar, "mmol" means millimole(s), "ppm" means parts per million, "wt" means weight, "wt %" means weight percent, "g" means grams, "µg" means micrograms, HPLC" means high performance liquid chromatography, "O.D." means optical density at the designated wavelength, "dcw" means dry cell weight, "CFU" means colony forming units, "ATCC" or "ATCC®" means the American Type Culture Collection (Manassas, Va.), "U" means units of perhydrolase activity, "rpm" means revolutions per minute, "EDTA" means ethylenediaminetetraacetic acid, "IPTG" means isopropyl β-D-1-thiogalactopyranoside, "ABTS" means 2,2'-azino-bis (3-ethylbenzothiazoline)-6-sulfonate. "CFU" means colony forming units, "XTT" means ((2,3-Bis-[2-methoxy-4-nitro-5-sulfophenyl]-2H-tetrazolium-5-carboxanilide inner salt; CAS# 111072-

31-2), and "CGSC" means *Coli* Genetic Stock Center (Yale University *Escherichia Coli* Genetic Stock Center, New Haven, Conn.).

EXAMPLE 1

Preparation of Cell Pastes

A single colony from a *Lactobacilli* MRS agar plate (Acumedia Manufacturing, Inc., Lansing, Mich.) was transferred to 10 mL *Lactobacilli* MRS broth (Hardy Diagnostic, Santa Maria, Calif.) and grown for 16-18 hours at 37° C. with shaking (250 rpm). One mL of this culture was used to inoculate 250 mL of fresh broth. Cells were grown at 37° C. with shaking (250 rpm) at 37° C. for 18-24 hours. Cells were harvested by centrifugation at 7,000 rpm for 20 minutes. Wet weight of cells was determined and cell pellet was frozen and stored at −70° C. This method may be scaled to 500 mL or larger as needed.

EXAMPLE 2

Peracid Production and Detection Assay at pH 6.5

This example describes a method that combines the production of peracid and the measurement of the amount of peracid produced. The assay was carried out in 96-well microtiter plates and analyzed using a SpectroMax® plus plate reader (Molecular Devices Corp.; Sunnyvale, Calif.) at 405 nm.

Oxidation of 2,2'-azino-bis-(3-ethylbenzothiazoline)-6-sulfonate (ABTS) was used to measure peracid concentration. Briefly, the enzyme catalyst was mixed with the substrate in the presence of hydrogen peroxide to produce the peracid. The amount of peracid produced was determined by mixing the peracid with ABTS. The concentration of the oxidized ABTS was measured spectrophotometrically at 405 nm in microtiter plates.

Whole cell paste was suspended in 0.1M $KH_2PO_4$ buffer (pH 6.5) at a final concentration ranging from 0.04 mg/mL to 4.0 mg/mL wet cell weight. A mixture of 100 μL of cell suspension, 30 μL of 0.1 M phosphate buffer (pH 6.5), 20 μL of 313 mM hydrogen peroxide and 50 μL of 200 mM substrate were incubated at 37° C. for 15 minutes to 24 hr. Control samples were prepared by omitting hydrogen peroxide from the reaction mixture, and substituting an equivalent volume of deionized water. The reaction mixture was assayed by mixing 100 μL of the supernatant from a centrifuged reaction mixture with 50 μL of 1.5 M acetic acid containing 0.03 mg/mL potassium iodide and 50 μL of 1 mg/mL 2,2'-azino-bis-(3-ethylbenzothiazoline)-6-sulfonate (ABTS) in a microtiter plate well, incubating at room temperature for 10 minutes, and measuring the absorbance of the assay mixture at 405 nm.

EXAMPLE 3

Peracid Production and Detection Assay at pH 4.0

This example describes a method that combines the production of peracid and the measurement of the amount of peracid produced. The assay was carried out in 96 well microtiter plates and analyzed using a SpectroMax® plus plate reader at 405 nM.

Whole cell paste was suspended in 0.1 M sodium acetate buffer (pH 4.0) at a final concentration ranging from 0.04 mg/mL to 4.0 mg/mL wet cell weight. A mixture of 100 μL of cell suspension, 30 μL of 0.1 M acetate buffer (pH 4.0), 20 μL of 313 mM hydrogen peroxide and 50 μL of 200 mM substrate were incubated at 37° C. for 15 minutes to 24 hours. Control samples were prepared by omitting hydrogen peroxide from the reaction mixture, and substituting an equivalent volume of deionized water. The reaction mixture was assayed by mixing 100 μL of the supernatant from a centrifuged reaction mixture with 50 μL of 1.5 M acetic acid containing 0.03 mg/mL potassium iodide and 50 μL of 1 mg/mL 2,2'-azino-bis-(3-ethylbenzothiazoline)-6-sulfonate (ABTS) in a microtiter plate well, incubating at room temperature for 10 minutes, and measuring the absorbance of the assay mixture at 405 nm.

EXAMPLE 4

Production of Peracetic Acid by Perhydrolysis of Triacetin with Hydrogen Peroxide at pH 6.5 Using *Lactobacillus* sp.

Following the method for analysis of peracid production described in Example 2, the following *Lactobacillus* sp. (0.2 mg/mL) were assayed for perhydrolytic activity using triacetin and hydrogen peroxide and a reaction time of 15 min (Table 1). Controls for each *Lactobacillus* sp. assayed were run with no added $H_2O_2$, and produced no detectable peracetic acid.

TABLE 1

| Peracid generation at pH 6.5 with triacetin as substrate | | |
|---|---|---|
| *Lactobacillus* sp. (ATCC catalog number) | pH | Peracetic Acid Concentration (ppm) in 15 min |
| *L. plantarum* (ATCC BAA793) | 6.5 | 5.7 |
| *L. casei* (ATCC 4646) | 6.5 | 4.9 |
| *L. paracasei* (ATCC 11974) | 6.5 | 5.5 |
| *L. fermentum* (ATCC 11976) | 6.5 | 4.2 |
| *L. rhamnosus* (ATCC 21052) | 6.5 | 4.5 |
| *L. crispatus* (ATCC 33197) | 6.5 | 5.5 |
| *L. amylovorus* (ATCC 33198) | 6.5 | 5.4 |
| *L. gallinarum* (ATCC 33199) | 6.5 | 5.5 |
| Control (no $H_2O_2$) | 6.5 | 0.0 |

EXAMPLE 5

Production of Peracetic Acid by Perhydrolysis of Ethyl Acetate with Hydrogen Peroxide at pH 6.5 Using *Lactobacillus* sp.

Following the method for analysis of peracid production described in Example 2, the following *Lactobacillus* sp. (0.2 mg/mL) were assayed for perhydrolytic activity using ethyl acetate and hydrogen peroxide and a reaction time of 15 min (Table 2). Controls for each *Lactobacillus* sp. assayed were run with no added $H_2O_2$, and produced no detectable peracetic acid.

TABLE 2

Peracid generation at pH 6.5 with ethyl acetate as substrate

| Lactobacillus sp. (ATCC Catalog Number) | pH | Peracetic acid concentration (ppm) in 15 min |
|---|---|---|
| L. plantarum (ATCC BAA793) | 6.5 | 2.4 |
| L. casei (ATCC 4646) | 6.5 | 2.4 |
| L. paracasei (ATCC 11974) | 6.5 | 2.5 |
| L. fermentum (ATCC 11976) | 6.5 | 1.8 |
| L. rhamnosus (ATCC 21052) | 6.5 | 1.6 |
| L. crispatus (ATCC 33197) | 6.5 | 1.9 |
| L. amylovorus (ATCC 33198) | 6.5 | 2.0 |
| L. gallinarum (ATCC 33199) | 6.5 | 1.7 |
| Control (no $H_2O_2$) | 6.5 | 0.0 |

EXAMPLE 6

Production of Peracetic Acid by Perhydrolysis of Triacetin with Hydrogen Peroxide at pH 4.0 Using *Lactobacillus* sp.

Following the method for analysis of peracid production described in Example 3, the following *Lactobacillus* sp. (2.0 mg/mL) were assayed for perhydrolytic activity using triacetin and hydrogen peroxide and a reaction time of 15 min (Table 3). Controls for each *Lactobacillus* sp. assayed were run with no added $H_2O_2$, and produced no detectable peracetic acid.

TABLE 3

Peracid generation at pH 4.0 with triacetin as substrate

| Lactobacillus sp. (ATCC Catalog Number) | pH | Peracetic acid concentration (ppm) in 15 min |
|---|---|---|
| L. plantarum (ATCC BAA793) | 4.0 | 8.3 |
| L. casei (ATCC 4646) | 4.0 | 7.5 |
| L. paracasei (ATCC 11974) | 4.0 | 4.3 |
| L. fermentum (ATCC 11976) | 4.0 | 7.6 |
| L. rhamnosus (ATCC 21052) | 4.0 | 6.3 |
| L. crispatus (ATCC 33197) | 4.0 | 7.8 |
| L. amylovorus (ATCC 33198) | 4.0 | 7.5 |
| L. gallinarum (ATCC 33199) | 4.0 | 5.6 |
| Control (no $H_2O_2$) | 4.0 | 0 |

EXAMPLE 7

Production of Perlactic Acid by Perhydrolysis of Ethyl Lactate with Hydrogen Peroxide at pH 6.5 Using *Lactobacillus* sp.

Following the method for analysis of peracid production described in Example 2, the following *Lactobacillus* sp. (0.2 mg/mL) were assayed for perhydrolytic activity using ethyl lactate and hydrogen peroxide and a reaction time of 15 min (Table 4). Controls for each *Lactobacillus* sp. assayed were run with no added $H_2O_2$, and produced no detectable perlactic acid.

TABLE 4

Peracid generation at pH 6.5 with ethyl lactate as substrate

| Lactobacillus sp. (ATCC Catalog Number) | pH | Perlactic acid concentration (ppm) in 15 min |
|---|---|---|
| L. plantarum (ATCC BAA793) | 6.5 | 1.1 |
| L. casei (ATCC 4646) | 6.5 | 1.0 |
| L. paracasei (ATCC 11974) | 6.5 | 1.1 |
| L. fermentum (ATCC 11976) | 6.5 | 0.73 |
| L. rhamnosus (ATCC 21052) | 6.5 | 0.75 |
| L. crispatus (ATCC 33197) | 6.5 | 1.2 |
| L. amylovorus (ATCC 33198) | 6.5 | 1.0 |
| L. gallinarum (ATCC 33199) | 6.5 | 1.3 |
| Control (no $H_2O_2$) | 6.5 | 0.0 |

EXAMPLE 8

Production of Peracetic Acid by Perhydrolysis of Ethyl Acetate with Hydrogen Peroxide at pH 4.0 Using *Lactobacillus* sp.

Following the method for analysis of peracid production described in Example 3, the following *Lactobacillus* sp. (0.2 mg/mL) were assayed for perhydrolytic activity using ethyl acetate and hydrogen peroxide and a reaction time of 15 min (Table 5). Controls for each *Lactobacillus* sp. assayed were run with no added $H_2O_2$, and produced no detectable peracetic acid.

TABLE 5

Peracid generation at pH 4.0 with ethyl acetate as substrate

| Lactobacillus sp. (ATCC Catalog Number) | pH | Peracetic acid concentration (ppm) in 15 min |
|---|---|---|
| L. plantarum (ATCC BAA793) | 4.0 | 1.3 |
| L. casei (ATCC 4646) | 4.0 | 1.3 |
| L. paracasei (ATCC 11974) | 4.0 | 1.7 |
| L. fermentum (ATCC 11976) | 4.0 | 1.3 |
| L. rhamnosus (ATCC 21052) | 4.0 | 1.4 |

TABLE 5-continued

Peracid generation at pH 4.0 with ethyl acetate as substrate

| Lactobacillus sp. (ATCC Catalog Number) | pH | Peracetic acid concentration (ppm) in 15 min |
|---|---|---|
| L. crispatus (ATCC 33197) | 4.0 | 1.4 |
| L. amylovorus (ATCC 33198) | 4.0 | 1.3 |
| L. gallinarum (ATCC 33199) | 4.0 | 1.3 |
| Control (no $H_2O_2$) | 4.0 | 0.0 |

EXAMPLE 9

Production of Perlactic Acid by Perhydrolysis of Ethyl Lactate with Hydrogen Peroxide at pH 4.0 Using *Lactobacillus* sp.

Following the method for analysis of peracid production described in Example 3, the following *Lactobacillus* sp. (0.2 mg/mL) were assayed for perhydrolytic activity using ethyl lactate and hydrogen peroxide and a reaction time of 15 min (Table 6). Controls for each *Lactobacillus* sp. assayed were run with no added $H_2O_2$, and produced no detectable perlactic acid.

TABLE 6

Peracid generation at pH 4.0 with ethyl lactate as substrate

| Lactobacillus sp. (ATCC Catalog Number) | pH | Perlactic acid concentration (ppm) in 15 min |
|---|---|---|
| L. plantarum (ATCC BAA793) | 4.0 | 1.3 |
| L. casei (ATCC 4646) | 4.0 | 1.3 |
| L. paracasei (ATCC 11974) | 4.0 | 1.3 |
| L. fermentum (ATCC 11976) | 4.0 | 1.3 |
| L. rhamnosus (ATCC 21052) | 4.0 | 1.3 |
| L. crispatus (ATCC 33197) | 4.0 | 1.3 |
| L. amylovorus (ATCC 33198) | 4.0 | 1.3 |
| L. gallinarum (ATCC 33199) | 4.0 | 1.2 |
| Control (no $H_2O_2$) | 4.0 | 0.0 |

EXAMPLE 10

Preparation of *Lactobacillus* sp. Cell Extracts

In a typical procedure, a frozen seed stock bead (Microbank™, Pro-Lab Diagnostics Austin, Tex.) was transferred to 5 mL of *Lactobacillus* MRS broth and grown for 16-18 hours at 36° C., static (no mixing). One mL of this culture was used to inoculate fresh broth containing 20 mM DL-threonine (EMScience, Gibbstown, N.J.) and either no triacetin or 50 mM triacetin. Growth was at 36° C., static. Cells were harvested by centrifugation while in log phase of growth, and washed twice in ice cold deionized water. The recovered paste was either stored frozen at −70° C. or used immediately. Cell paste (1 g wet weight cells) was suspended in 5 mL of Novagen® BugBuster® Master Mix (EMD Biosciences, Inc.), and the mixture incubated at 36° C. for 3-4 hours with gentle shaking. The mixture was then subjected to two passes through a French® Pressure Cell Press and the extract centrifuged at 12,000 rpm for 2 minutes (Eppendorf, North American). The resulting supernatant was collected and tested for perhydrolytic activity.

EXAMPLE 11

Peracid Production at pH 6.5 Using *Lactobacillus* sp. Whole Cells

Cells grown according to the procedure in Example 1 were suspended in 0.05 M phosphate buffer ($KH_2PO_4$, pH 6.5) at 40 mg (wet cell weight)/mL concentration. To a 100-µL aliquot of 40 mg (wet cell weight)/mL cell suspension was added 900 µL of substrate (277 mM triacetin) and 26 µL of 30% hydrogen peroxide (500 mM) at room temperature with vigorous stirring. Controls without enzyme were run concurrently. After stirring for 5 or 30 minutes, a 0.250 mL sample was filtered using a 30,000 Nominal Molecular Weight Limit (NMWL) filter (Millipore UltraFree-MC, Millipore Corp., Billerica, Mass.) centrifuged for 2 minutes at 12,000 RPM. A portion of the filtered reaction samples was diluted 1:10 with dd water and analyzed for hydrogen peroxide, and the remaining portion of the sample was directly analyzed for peracid using the HPLC assay method. The following *Lactobacillus* sp. were assayed (Table 7) for peracid generation.

TABLE 7

Peracid generation at pH 6.5 with triacetin as substrate 5 and 30 minutes

| Lactobacillus sp. (ATCC Catalog Number) | pH | Peracetic acid concentration (ppm) in 5 min | Peracetic acid concentration (ppm) in 30 min |
|---|---|---|---|
| L. plantarum (ATCC BAA793) | 6.5 | 9.3 | 1.5 |
| L. casei (ATCC 4646) | 6.5 | 36 | 23.7 |
| L. paracasei (ATCC 11974) | 6.5 | 58.2 | 35.1 |
| L. crispatus (ATCC 33197) | 6.5 | 77.4 | 48.8 |
| L. gallinarum (ATCC 33199) | 6.5 | 91.8 | 48.7 |

EXAMPLE 12

Scale-Up of Peracid Production at pH 6.5 Using *Lactobacillus* sp. Whole Cells

The procedure described in Example 11 was repeated, except that the reaction was run at 10-mL scale, and the concentration of wet cells in the reaction was increased to 40 mg/mL. *Lactobacillus plantarum* BAA793 was assayed for perhydrolytic activity using 250 mM triacetin and 500 mM hydrogen peroxide (Table 8).

TABLE 8

Peracid generation at pH 6.5 with triacetin as substrate at 5 minutes

| Lactobacillus sp. (ATCC Catalog Number) | pH | Peracetic acid concentration (ppm) in 5 min |
|---|---|---|
| L. plantarum (ATCC BAA793) | 6.5 | 171 |

EXAMPLE 13

Peracid Production at pH 6.5 Using *Lactobacillus Plantarum* BAA793 Cell Extract Using the procedure described in Example 10, a cell extract of *Lactobacillus plantarum* BAA793 (100 µL) was prepared and substituted for the whole cell suspension in a reaction run as described in Example 11. Extracts were tested after 20 minutes and 180 minutes of extraction incubation, and assayed for perhydrolytic activity using 250 mM triacetin and 500 mM hydrogen peroxide (Table 9).

TABLE 9

Peracid generation at pH 6.5 with triacetin as substrate at 5 minutes

| Lactobacillus sp. (ATCC Catalog Number) | pH | Peracetic acid concentration (ppm) in 5 min |
|---|---|---|
| L. plantarum (ATCC BAA793) 20 min incubation | 6.5 | 256 |
| L. plantarum (ATCC BAA793) 180 min incubation | 6.5 | 277 |

EXAMPLE 14

Induction of Perhydrolytic Activity in *Lactobacillus* sp.

Cells were grown in the presence or absence of 50 mM triacetin as described in Example 10. Perhydrolytic activity of whole cells grown in the presence or absence of added triacetin was measured at pH 6.5 using the procedures described in Example 2 and Example 11 (Table 10).

TABLE 10

Peracid generation at pH 6.5 in 5 min with whole cells grown with and without triacetin and assayed with triacetin as substrate.

| Lactobacillus sp. (ATCC Catalog Number) | pH | mg wet cell wt/mL | Peracetic acid concentration (ppm) in 5 min; 50 mM triacetin/ 30 mM hydrogen peroxide | Peracetic acid concentration (ppm) in 5 min; 250 mM triacetin/500 mM hydrogen peroxide |
|---|---|---|---|---|
| L. plantarum (ATCC BAA793) No triacetin during growth | 6.5 | 1.0 | 4.0 | |
| L. gallinarum (ATCC 33199) No triacetin during growth | 6.5 | 1.0 | 3.8 | |
| L. plantarum (ATCC BAA793) 50 mM triacetin during growth | 6.5 | 1.0 | 16 | |
| L. gallinarum (ATCC 33199) 50 mM triacetin during growth | 6.5 | 1.0 | 16.8 | |
| L. plantarum (ATCC BAA793) 50 mM triacetin during growth | 6.5 | 40 | | 453 |

EXAMPLE 15

Comparision of Minimum Biocidal Concentration (MBC) of *Lactobacillus* sp.-Derived Peracetic Acid and Commercial Peracetic Acid The minimum biocidal concentration (MBC) of peracid required to produce a 5-log kill of *Staphylococcus aureus* ATCC 6538, *Salmonella cholerasuis* ATCC 10708 and *Pseudomonas aeruginosa* ATCC 15442 was determined according to the following procedure. Cultures were grown in 5 mL LB broth (Media Tech, Inc.) for 17-24 hours at 35° C. with shaking and subsequently plated on Trypticase Soy Agar (VWR). At least 3 consecutive daily transfers were made. Plates were incubated for 20-24 hours at 35° C.±2° C. Each culture was removed from the agar surface by flooding with 5-7 mL of phosphate buffer, pH 7.2. (e.g., Butterflies or equivalent) and transferred into a sterile flask. The $OD_{600}$ of the culture suspension was measured and the cell suspension was diluted in phosphate buffer to a final cell density between 1-2 E+05 and 1-2 E+06 CFU/mL, where the final cell concentration was adjusted to produce the concentration needed for the number of logs kill required. The peracetic acid solution to be tested was diluted by doubling dilutions from 600 ppm to 0.5 ppm in sterile water. Test inoculum (100 µL) was added each well of a 96-well microtiter plate, columns 1-11; column 12 was employed for a blank check using sterile dd water in place of inoculum. Decreasing concentrations of peracid solution (100 µL) was added across columns 1-10, and the plates held at room temperature for the required exposure time (e.g., 10 minutes). A Neutralization/detection plate was prepared with Letheen Broth (Difco #268110) and XTT (4 mM stock in water, 2,3-bis-[2-methoxy-4-nitro-5-sulfophenyl]-2H-tetrazolium-5-carboxanilide inner salt); 190 µL was added to each well of a fresh 96 well microtiter plate. From each well of the exposure plate, a 10 µL aliquot was transferred to the neutralization/detection plate. An $OD_{450}$ reading was measured, and the plate incubated at 35° C.±2° C. for 24 hours. A second $OD_{450}$ was measured, where orange color was indicative of cell growth. A suspension to test organism(s) was prepared equal to 1-2 E+04 CFU/mL. Add A 10 μL aliquot of this suspension was added to each negative well except column 12, and the plates incubated at 35° C.±2° C. for 24 hours. The OD$_{450}$ was measured, and the MBC corresponded to the first column (in order of decreasing concentration of peracetic acid) in which all wells in a column showed no growth (OD value same as blank). The MBC of peracetic acid generated enzymatically from triacetin by *Lactobacillus plantarum* ATCC BAA793 (Table 11) indicated equivalency with commercial peracetic acid.

TABLE 11

MBC in ppm PAA of enzymatically-generated peracetic acid from triacetin, and from commercial peracetic acid.

| Source of PAA | *Pseudomonas aeruginosa* ATCC 15442 | *Staphylococcus aureus* ATCC 6538 | *Salmonella cholerasuis* ATCC 10708 |
|---|---|---|---|
| Sigma Lot # 07726EC | 2.4-14 | 1.8-2.4 | 1.2-<2.4 |
| *L. plantarum* ATCC BAA793 | 1.4 | 1.4 | 1.4 |

What is claimed is:

1. A process for producing peroxycarboxylic acid from carboxylic acid ester substrates comprising
   a) providing a set of peracid reaction components, said components comprising:
      1) a carboxylic acid ester substrate selected from the group consisting of:
         i) esters having the structure

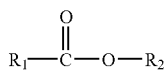

wherein R$_1$=C1 to C10 straight chain or branched chain alkyl optionally substituted with an hydroxyl or a C1 to C4 alkoxy group and R$_2$=C1 to C10 straight chain or branched chain alkyl group, (CH$_2$CH$_2$—O)$_n$H or (CH$_2$CH(CH$_3$)—O)$_n$H and n=1 to 10; and
      ii) glycerides having the structure

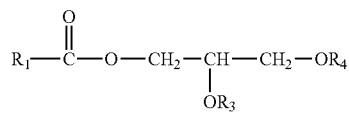

wherein R$_1$=C1 to C10 straight chain or branched chain alkyl optionally substituted with an hydroxyl or a C1 to C4 alkoxy group and R$_3$ and R$_4$ are individually H or R$_1$C(O); and
      2) a source of peroxygen; and
      3) at least one *Lactobacillus* sp. derived-catalyst having a perhydrolysis activity; and
   b) combining said reaction components under suitable aqueous reaction conditions, wherein said conditions comprise a pH range of about 2 to about 9, whereby a peroxycarboxylic acid is produced at a concentration of at least 500 ppb within about 5 minutes to about 2 hours of combining the reaction components.

2. The process of claim 1 wherein the pH is less than about 6.5.

3. The process of claim 2 wherein the pH range is less than about 4.5.

4. The process of any one of claims 1-3 wherein the ester substrate is selected from the group consisting of methyl lactate, ethyl lactate, methyl glycolate, ethyl glycolate, methyl methoxyacetate, ethyl methoxyacetate, methyl 3-hydroxybutyrate, ethyl 3-hydroxybutyrate, and mixtures thereof.

5. The process of any one of claims 1-3 wherein the glyceride substrate is selected from the group consisting of monoacetin, diacetin, triacetin, monopropionin, dipropionin, tripropionin, monobutyrin, dibutyrin, tributyrin, and mixtures thereof.

6. The process of claim 1 wherein the perhydrolysis activity is derived from a *Lactobacillus* sp. selected from the group consisting of *Lactobacillus plantarum, Lactobacillus casei, Lactobacillus paracasei, Lactobacillus fermentum, Lactobacillus rhamnosus, Lactobacillus crispatus, Lactobacillus amylovorus,* and *Lactobacillus gallinarum.*

7. The process of claim 6 wherein the perhydrolysis activity is derived from a *Lactobacillus* sp. selected from the group consisting of *Lactobacillus plantarum* (ATCC BAA793), *Lactobacillus casei* (ATCC 4646), *Lactobacillus paracasei* (ATCC 11974), *Lactobacillus fermentum* (ATCC 11976), *Lactobacillus rhamnosus* (ATCC 21052), *Lactobacillus crispatus* (ATCC 33197), *Lactobacillus amylovorus* (ATOC 33198), and *Lactobacillus gallinarum* (ATCC 33199).

8. The process of claim 1 wherein the peracid produced is selected from the group consisting of peracelic acid, perpropionic acid, perbutyric acid, perlactic acid, perglycolic acid, permethoxyacetic acid, per-β-hydroxybutyric acid, and mixtures thereof.

9. The process of claim 8 wherein the peracid produced is peracetic acid.

10. A process to reduce a microbial population on a hard surface or inanimate object using an enzymatically produced aqueous peracid composition, said process comprising:
   a) providing a set of peracid reaction components, said components comprising:
      1) a substrate selected from the group consisting of:
         i) esters having the structure

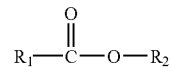

wherein R$_1$=C1 to C10 straight chain or branched chain alkyl optionally substituted with an hydroxyl or a C1 to C4 alkoxy group and R$_2$=C1 to C10 straight chain or branched chain alkyl group, (CH$_2$CH$_2$—O)$_n$H or (CH$_2$CH(CH$_3$)—O)$_n$H and n=1 to 10; and
      ii) glycerides having the structure

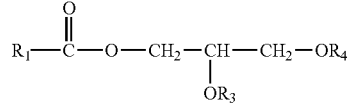

wherein $R_1$=C1 to C10 straight chain or branched chain alkyl optionally substituted with an hydroxyl or a C1 to C4 alkoxy group and $R_3$ and $R_4$ are individually H or $R_1C(O)$; and 2) a source of peroxygen; and
3) at least one *Lactobacillus* sp. derived-catalyst having a perhydrolysis activity;

b) providing a hard surface or an inanimate object having a concentration of microorganisms and/or viruses;

c) combining said reaction components under suitable aqueous reaction conditions said conditions comprising a pH range of about 2 to about 9, whereby a peracid product is formed having a peracid concentration of at least 1.5 ppm within about 5 minutes to about 2 hours of combining the reaction components;

d) optionally diluting said peracid product; and e) contacting said hard s surface or said inanimate object with the peracid produced in step c) or step d) within about 48 hours of combining said reaction components whereby the concentration of said microorganisms and/or viruses is reduced at least 3-log.

11. The process of claim 10 wherein the hard surface or the inanimate object is contacted with the peracid produced in step c) or step d) within about 2 hours of combining said reaction components.

12. The process of claim 11 wherein the hard surface or the inanimate object is contacted with the peracid produced in step c) or step d) within about 30 minutes of combining said reaction components.

13. The process according to any one of claims 10-12 wherein the concentration of said microorganisms and/or viruses is reduced at least 5-log.

14. The process of claim 10 wherein the pH range is less than about 6.5.

15. The process of claim 14 wherein the pH range is less than about 4.5.

16. The process of claim 10 wherein the ester substrate is selected from the group consisting of methyl lactate, ethyl lactate, ethyl acetate, methyl glycolate, ethyl glycolate, methyl methoxyacetate, ethyl methoxyacetate, methyl 3-hydroxybutyrate, ethyl 3-hydroxybutyrate, and mixtures thereof.

17. The process of claim 16 wherein the ester substrate is selected from the group consisting of ethyl lactate, ethyl acetate, and mixtures thereof.

18. The process of claim 10 wherein the glyceride substrate is selected from the group consisting of monoacetin, diacetin, triacetin, monopropionin, dipropionin, tripropionin, monobutryin, dibutyrin, tributyrin, and mixtures thereof.

19. The process of claim 10 wherein the perhydrolysis activity is derived from a *Lactobacillus* sp. selected from the group consisting of *Lactobacillus plantarum, Lactobacillus casei, Lactobacillus paracasei, Lactobacillus fermentum, Lactobacillus rhamnosus, Lactobacillus crispatus, Lactobacillus amylovorus,* and *Lactobacillus gallinarurm.*

20. The process of claim 19 wherein the perhydrolysis activity is derived from a *Lactobacillus* sp. selected from the group consisting of *Lactobacillus plantarum* (ATCC BAA793), *Lactobacillus casei* (ATCC 4646), *Lactobacillus paracasei* (ATCC 11974), *Lactobacillus fermentum* (ATCC 11976), *Lactobacillus rhamnosus* (ATCC 21052), *Lactobacillus crispatus* (ATCC 33197), *Lactobacillus amylovorus* (ATCC 33198), and *Lactobacillus gallinarum* (ATCC 33199).

21. The process of claim 20 wherein the peracid is produced at a concentration of at least 2.5 ppm within about 2 hours.

22. The process of claim 21 wherein the peracid is produced at a concentration of at least 4.5 ppm within about 2 hours.

23. The process of claim 22 wherein the peracid is produced at a concentration of at least 7.5 ppm within about 2 hours.

24. The process of claim 10 wherein the peracid produced is selected from the group consisting of peracetic acid, perpropionic acid, perbutyric acid, perlactic acid, perglycolic acid, permethoxyacetic acid, per-β-hydroxybutyric acid, and mixtures thereof.

25. The process according to claim 24 wherein the peracid produced is peracetic acid.

26. The process of any one of claims 1-3 wherein the ester substrate is ethyl acetate.

* * * * *